United States Patent
Hanina et al.

(10) Patent No.: US 9,875,666 B2
(45) Date of Patent: Jan. 23, 2018

(54) APPARATUS AND METHOD FOR RECOGNITION OF PATIENT ACTIVITIES

(75) Inventors: Adam Hanina, New York, NY (US); Gordon Kessler, Mt. Kisco, NY (US); Lei Guan, Philadelphia, PA (US)

(73) Assignee: AIC Innovations Group, Inc., New York, NY (US)

(*) Notice: Subject to any disclaimer, the term of this patent is extended or adjusted under 35 U.S.C. 154(b) by 164 days.

(21) Appl. No.: 13/235,387

(22) Filed: Sep. 18, 2011

(65) Prior Publication Data

US 2012/0009555 A1    Jan. 12, 2012

Related U.S. Application Data

(63) Continuation-in-part of application No. 12/815,037, filed on Jun. 14, 2010, now Pat. No. 9,293,060.

(60) Provisional application No. 61/498,576, filed on Jun. 19, 2011, provisional application No. 61/331,872, filed on May 6, 2010.

(51) Int. Cl.
| | |
|---|---|
| *G09B 23/28* | (2006.01) |
| *H04N 7/18* | (2006.01) |
| *G09B 19/00* | (2006.01) |
| *G06F 19/00* | (2011.01) |

(52) U.S. Cl.
CPC ......... *G09B 19/00* (2013.01); *G06F 19/3456* (2013.01)

(58) Field of Classification Search
CPC .................................. G09B 19/00; G06F 1/00
USPC ......................................................... 434/365
See application file for complete search history.

(56) References Cited

U.S. PATENT DOCUMENTS

| | | | |
|---|---|---|---|
| 3,814,845 A | 6/1974 | Hurlbrink et al. | |
| 5,065,447 A | 11/1991 | Barnsley et al. | |
| 5,441,047 A | 8/1995 | David et al. | |
| 5,486,001 A * | 1/1996 | Baker ........................... | 473/266 |
| 5,544,649 A | 8/1996 | David et al. | |
| 5,544,661 A | 8/1996 | Davis et al. | |
| 5,564,429 A | 10/1996 | Bornin | |
| 5,619,991 A | 4/1997 | Sloane | |
| 5,646,912 A | 7/1997 | Cousin | |
| 5,752,621 A | 5/1998 | Passamante | |
| 5,764,296 A | 6/1998 | Shin | |
| 5,810,747 A * | 9/1998 | Brudny et al. ................ | 600/595 |

(Continued)

FOREIGN PATENT DOCUMENTS

| | | |
|---|---|---|
| WO | WO 2008/070759 | 6/2008 |
| WO | WO 2011/062934 | 5/2011 |

OTHER PUBLICATIONS

Non-Final Office Action from PTO, U.S. Appl. No. 12/620,686, (dated Dec. 21, 2011),1-78.

(Continued)

*Primary Examiner* — Sam Yao
*Assistant Examiner* — Alvin Carlos
(74) *Attorney, Agent, or Firm* — Fish & Richardson P.C.

(57) ABSTRACT

A medication confirmation method and apparatus. The method of an embodiment of the invention includes the steps of capturing one or more video sequences of a user administering medication via a medication administration apparatus, storing the captured one or more video sequences, and analyzing at least one of the stored video sequences to confirm that the user has properly administered the medication, and has properly positioned the medication administration apparatus.

27 Claims, 7 Drawing Sheets

(56) References Cited

U.S. PATENT DOCUMENTS

| | | | |
|---|---|---|---|
| 5,911,132 A * | 6/1999 | Sloane | 705/3 |
| 5,961,446 A * | 10/1999 | Beller et al. | 600/300 |
| 6,126,449 A * | 10/2000 | Burns | 434/252 |
| 6,141,584 A | 10/2000 | Rockwell et al. | |
| 6,151,521 A * | 11/2000 | Guo et al. | 600/407 |
| 6,154,558 A | 11/2000 | Hsieh | |
| 6,233,428 B1 * | 5/2001 | Fryer | 434/308 |
| 6,283,761 B1 | 9/2001 | Joao | |
| 6,302,844 B1 | 10/2001 | Walker | |
| 6,327,497 B1 | 12/2001 | Kirchgerog et al. | |
| 6,380,858 B1 | 4/2002 | Yarin et al. | |
| 6,409,661 B1 * | 6/2002 | Murphy | 600/300 |
| 6,421,650 B1 | 7/2002 | Goetz et al. | |
| 6,461,162 B1 * | 10/2002 | Reitman | G06F 19/3481 434/118 |
| 6,483,993 B1 | 11/2002 | Misumi et al. | |
| 6,484,144 B2 | 11/2002 | Martin et al. | |
| 6,535,637 B1 | 3/2003 | Wootton et al. | |
| 6,611,206 B2 * | 8/2003 | Eshelman et al. | 340/573.1 |
| 6,705,991 B2 | 3/2004 | Bardy | |
| 6,879,970 B2 * | 4/2005 | Shiffman | G06F 19/327 706/21 |
| 6,988,075 B1 | 1/2006 | Hacker | |
| 7,184,047 B1 | 2/2007 | Crampton | |
| 7,184,075 B2 | 2/2007 | Reiffel | |
| 7,256,708 B2 * | 8/2007 | Rosenfeld et al. | 340/870.01 |
| 7,277,752 B2 * | 10/2007 | Matos | 607/5 |
| 7,304,228 B2 | 12/2007 | Bryden et al. | |
| 7,307,543 B2 | 12/2007 | Rosenfeld et al. | |
| 7,317,967 B2 | 1/2008 | DiGianfilippo et al. | |
| 7,340,077 B2 | 3/2008 | Gokturk | |
| 7,369,919 B2 | 5/2008 | Vonk et al. | |
| 7,395,214 B2 | 7/2008 | Shillingburg | |
| 7,415,447 B2 | 8/2008 | Shiffman et al. | |
| 7,448,544 B1 | 11/2008 | Louie et al. | |
| 7,562,121 B2 * | 7/2009 | Berisford et al. | 709/206 |
| 7,627,142 B2 | 12/2009 | Kurzweil et al. | |
| 7,657,443 B2 | 2/2010 | Crass et al. | |
| 7,692,625 B2 | 4/2010 | Morrison et al. | |
| 7,740,013 B2 | 6/2010 | Ishizaki et al. | |
| 7,747,454 B2 | 6/2010 | Bartfeld et al. | |
| 7,761,311 B2 | 7/2010 | Clements et al. | |
| 7,769,465 B2 * | 8/2010 | Matos | 607/60 |
| 7,774,075 B2 | 8/2010 | Lin et al. | |
| 7,840,277 B2 | 11/2010 | Matos | |
| 7,874,984 B2 | 1/2011 | Elsayed et al. | |
| 7,881,537 B2 | 2/2011 | Ma et al. | |
| 7,908,155 B2 | 3/2011 | Fuerst et al. | |
| 7,912,733 B2 * | 3/2011 | Clements et al. | 705/2 |
| 7,956,727 B2 | 6/2011 | Loncar | |
| 7,983,933 B2 | 7/2011 | Karkanias et al. | |
| 8,321,284 B2 | 11/2012 | Clements et al. | |
| 8,702,606 B2 | 4/2014 | Wang et al. | |
| 2001/0049673 A1 | 12/2001 | Dulong et al. | |
| 2001/0056358 A1 | 12/2001 | Dulong et al. | |
| 2002/0026330 A1 * | 2/2002 | Klein | G06Q 10/10 705/3 |
| 2002/0093429 A1 | 7/2002 | Matsushita et al. | |
| 2002/0143563 A1 * | 10/2002 | Hufford | G06F 19/325 705/7.38 |
| 2003/0164172 A1 | 9/2003 | Chumas et al. | |
| 2003/0190076 A1 | 10/2003 | Delean | |
| 2003/0225325 A1 | 12/2003 | Kagermeier et al. | |
| 2004/0100572 A1 | 5/2004 | Kim | |
| 2004/0107116 A1 | 6/2004 | Brown | |
| 2004/0155780 A1 | 8/2004 | Rapchak | |
| 2004/0168951 A1 | 9/2004 | Mackie | |
| 2005/0144150 A1 | 6/2005 | Ramamurthy et al. | |
| 2005/0149361 A1 | 7/2005 | Saus et al. | |
| 2005/0180610 A1 | 8/2005 | Kato et al. | |
| 2005/0182664 A1 | 8/2005 | Abraham-Fuchs et al. | |
| 2005/0234381 A1 | 10/2005 | Niemetz et al. | |
| 2005/0267356 A1 | 12/2005 | Ramasubramanian et al. | |
| 2006/0066584 A1 | 3/2006 | Barkan | |
| 2006/0218011 A1 | 9/2006 | Walker et al. | |
| 2006/0238549 A1 | 10/2006 | Marks | |
| 2007/0008112 A1 | 1/2007 | Covannon et al. | |
| 2007/0008113 A1 | 1/2007 | Spoonhower et al. | |
| 2007/0016443 A1 | 1/2007 | Wachman et al. | |
| 2007/0030363 A1 | 2/2007 | Cheatle et al. | |
| 2007/0118054 A1 | 5/2007 | Pinhas et al. | |
| 2007/0118389 A1 * | 5/2007 | Shipon | 705/1 |
| 2007/0194034 A1 | 8/2007 | Vasiadis | |
| 2007/0233035 A1 | 10/2007 | Wehba et al. | |
| 2007/0233049 A1 | 10/2007 | Wehba et al. | |
| 2007/0233050 A1 | 10/2007 | Wehba et al. | |
| 2007/0233281 A1 | 10/2007 | Wehba et al. | |
| 2007/0233520 A1 | 10/2007 | Wehba et al. | |
| 2007/0233521 A1 * | 10/2007 | Wehba | A61M 5/142 705/3 |
| 2007/0265880 A1 | 11/2007 | Bartfeld et al. | |
| 2007/0273504 A1 | 11/2007 | Tran | |
| 2007/0276270 A1 | 11/2007 | Tran | |
| 2008/0000979 A1 | 1/2008 | Poisner | |
| 2008/0162192 A1 | 3/2008 | Vonk et al. | |
| 2008/0086533 A1 | 4/2008 | Neuhauser et al. | |
| 2008/0093447 A1 | 4/2008 | Johnson et al. | |
| 2008/0114226 A1 | 5/2008 | Music et al. | |
| 2008/0114490 A1 | 5/2008 | Jean-Pierre | |
| 2008/0138604 A1 | 6/2008 | Kenney et al. | |
| 2008/0140444 A1 | 6/2008 | Karkanias et al. | |
| 2008/0178126 A1 * | 7/2008 | Beeck | G06F 3/017 715/863 |
| 2008/0201174 A1 * | 8/2008 | Ramasubramanian et al. | 705/3 |
| 2008/0219493 A1 | 9/2008 | Tadmor | |
| 2008/0238666 A1 | 10/2008 | Loncar | |
| 2008/0275738 A1 | 11/2008 | Shillingburg | |
| 2008/0279420 A1 | 11/2008 | Masticola et al. | |
| 2008/0281630 A1 | 11/2008 | Sekura | |
| 2008/0290168 A1 | 11/2008 | Sullivan et al. | |
| 2008/0297589 A1 | 12/2008 | Kurtz et al. | |
| 2008/0303638 A1 | 12/2008 | Nguyen et al. | |
| 2009/0012818 A1 | 1/2009 | Rodgers | |
| 2009/0018867 A1 | 1/2009 | Reiner | |
| 2009/0024112 A1 | 1/2009 | Edwards et al. | |
| 2009/0043610 A1 | 2/2009 | Nadas et al. | |
| 2009/0048871 A1 | 2/2009 | Skomra | |
| 2009/0058635 A1 | 3/2009 | LaLonde et al. | |
| 2009/0095837 A1 | 4/2009 | Lindgren | |
| 2009/0128330 A1 | 5/2009 | Monroe | |
| 2009/0159714 A1 | 6/2009 | Coyne, III et al. | |
| 2009/0217194 A1 | 8/2009 | Martin et al. | |
| 2009/0245655 A1 | 10/2009 | Matsuzaka | |
| 2010/0042430 A1 | 2/2010 | Bartfeld | |
| 2010/0050134 A1 | 2/2010 | Clarkson | |
| 2010/0057646 A1 | 3/2010 | Martin et al. | |
| 2010/0092093 A1 | 4/2010 | Akatsuka et al. | |
| 2010/0136509 A1 | 6/2010 | Mejer et al. | |
| 2010/0138154 A1 | 6/2010 | Kon | |
| 2010/0255598 A1 | 10/2010 | Melker | |
| 2010/0262436 A1 | 10/2010 | Chen et al. | |
| 2010/0316979 A1 | 12/2010 | Von Bismarck | |
| 2011/0021952 A1 | 1/2011 | Vallone | |
| 2011/0119073 A1 | 5/2011 | Hanina et al. | |
| 2011/0141009 A1 | 6/2011 | Izumi | |
| 2011/0153360 A1 | 6/2011 | Hanina et al. | |
| 2011/0161109 A1 | 6/2011 | Pinsonneault et al. | |
| 2011/0195520 A1 | 8/2011 | Leider et al. | |
| 2011/0275051 A1 | 11/2011 | Hanina et al. | |
| 2012/0009555 A1 * | 1/2012 | Hanina | G06F 19/3456 434/262 |
| 2012/0075464 A1 | 3/2012 | Derenne et al. | |
| 2012/0121729 A1 | 5/2012 | Paterson et al. | |
| 2012/0316897 A1 | 12/2012 | Hanina et al. | |
| 2013/0044196 A1 | 2/2013 | Guan et al. | |

OTHER PUBLICATIONS

Final Office Action from PTO, U.S. Appl. No. 12/620,686, (dated May 8, 2012), 1-24.

International Preliminary Report on Patentability, (PCT/US2010/056935) (dated May 31, 2012), 1-8.

(56) References Cited

OTHER PUBLICATIONS

Non-Final Office Action from PTO, (U.S. Appl. No. 12/646 383), (dated Dec. 22, 2011),1-78.
Final Office Action from PTO, (U.S. Appl. No. 12/646 383), (dated May 8, 2012), 1-31.
Final Office Action from PTO, (U.S. Appl. No. 12/646,603), (dated Feb. 1, 2012), 1-17.
Non Final Office Action from PTO, (U.S. Appl. No. 12/728,721), (dated Jan. 6, 2012), 1-31.
Final Office Action from PTO, (U.S. Appl. No. 12/728,721), (dated Apr. 12, 2012), 1-31.
Non-Final Office Action from PTO, (U.S. Appl. No. 12/815,037), (dated Mar. 28, 2012),1-17.
PCT Search report and written opinion, (PCT/US2011/35093, (dated Sep. 12, 2011),1-8.
Non-Final Office Action from PTO, (U.S. Appl. No. 12/898,338), (dated Jun. 19, 2012), 1-16.
PCT Search report and written opinion, (PCT/US12/41785, (dated Aug. 17, 2012),1-10.
Danya, "Pilot Study Using Video Call Phones for Mobile Direct Observation Treatment (MDOT) to Monitor Medication Compliance of TB Patients", www.danya.com/MDOT.asp, (Mar. 20, 2009).
Guideline, "2008 Patient Adherence Update: New Approaches for Success", www.guideline.com, The Trend Report Series,(Oct. 1, 2008).
Guideview, "GuideView", www.sahs.uth.tme.edu/MSriram/GuideView/, (Mar. 15, 2007).
Osterberg, Lars et al., "Adherence to Medication", *N Engl J Med* 2005;353:487-97, (Aug. 4, 2005).
Chen, Pauline W., "Texting as a Health Tool for Teenagers", *The New York Times* http://www.nytimes.com/2009/11/05/health//05chen.html?_r=1&emc=, (Nov. 5, 2009).
"Global Tuberculosis Control: A short update to the 2009 report", *World Health Organization*, (2009).
"Super-Resolution", *Wikipedia*, (Oct. 5, 2010).
"PCT Search report and written opinion", (dated Jan. 12, 2011),1-9.
"Non-Final Office Action from PTO", (dated Oct. 13, 2011),1-74.
Non-Final Office Action from PTO, (U.S. Appl. No. 13/558,377), (dated Oct. 22, 2012), 1-21.
Final Office Action from PTO, (U.S. Appl. No. 13/558 377), dated May 7, 2013, 1-29.
Non-Final Office Action from PTO, (U.S. Appl. No. 13/558,380), (dated Oct. 4, 2012), 1-20.
Wang et al. "Recent Developments in human motion analysis." Pattern Recognition 36 (220) 585-601 (Nov. 2001).
Final Office Action from PTO, (U.S. Appl. No. 13/588,380), (dated Mar. 1, 2013), 1-27.
Non-Final Office Action from PTO, (U.S. Appl. No. 12/646,603), (dated Jun. 13, 2013), 1-16.
Non-Final Office Action from PTO, (U.S. Appl. No. 12/728 721), (dated May 9, 2013), 1-25.
Final Office Action from PTO, (U.S. Appl. No. 12/815,037), (dated Sep. 13, 2012), 1-15.
Non-Final Office Action from PTO, (U.S. Appl. No. 12/815,037), (dated Jul. 18, 2013), 1-19.
Non-Final Office Action from PTO, (U.S. Appl. No. 12/899 510), (dated Jan. 23, 2013), 1-20.
Final Office Action from PTO, (U.S. Appl. No. 12/899,510), (dated Aug. 20, 2013).
PCT Search report and written opinion, (PCT/US11/54666), (dated Feb. 28, 2012), 1-13.
Final Office Action from PTO, (U.S. Appl. No. 12/898 338), (dated Nov. 9, 2012), 1-12.
PCT Search report and written opinion, (PCT/US11/54668), dated Feb. 28, 2012, 1-12.
Non-Final Office Action from PTO, (U.S. Appl. No. 13/189 518), (dated Dec. 21, 2012), 1-10.
Final Office Action from PTO, (U.S. Appl. No. 13/189,518), (dated Jul. 23, 2013), 1-16.
PCT Search report and written opinion, (PCT/US12/42843), (dated Aug. 31, 2012), 1-8.
PCT Search report and written opinion, (PCT/US2012/051554), (dated Oct. 19, 2012), 1-12.
Huynh et al., "Real time detection, tracking and recognition of medication intake." World Academy of Science, Engineering and Technology 60 (2009), 280-287.
PCT Search report and written opinion, (PCT/US12/59139), (dated Dec. 18, 2012), 1-15.
PCT Search report and written Opinion, (PCT/US13/20026), (dated Aug. 5, 2013), 1-14.
Ammouri, S.; Biloduau, G. -A, "Face and Hands Detectionand Tracking Applied to the Monitoring of Medication Intake," Computer and Robot Vision, 2008. CRV '08. Canadian Conference on, vol. No., pp. 147, 154, May 28-30, 2008.
Batz, et al. "A computer Vision System for Monitoring Medicaiton Intake," in Proc. IEEE 2nd Canadian Conf. on Computer and Robot Vision, Victoria, BC, Canada, 2005, pp. 362-369.
Valin, et al. "Video Surveillance of Medication intake", Int. Conf. of the IEEE Engineering in Medicine and Biology Society, New York City, USA, Aug. 2006.
Bilodeau et al. Monitoring of Medication Intake Using a Camera System. Journal of Medical Systems 2011. [retrieved on Feb. 18, 2013] Retrieved from ProQuest Technology Collection.
Mintchell, "Exploring the Limits of Machine Vision", Automating World, Oct. 1, 2011.
U.S. Appl. No. 12/815,037, filed Jun. 14, 2010, Hanina et al.
U.S. Appl. No. 15/048,798, filed Feb. 19, 2016, Hanina et al.
U.S. Appl. No. 13/674,459, filed Nov. 12, 2012, Hanina et al.
U.S. Appl. No. 13/831,555, filed Mar. 14, 2013, Hanina et al.
EPO Supplementary European Search Report for EP 14770974, dated Aug. 22, 2016 (2 pages).

\* cited by examiner

APPARATUS AND METHOD FOR RECOGNITION OF PATIENT ACTIVITIES

CROSS REFERENCE TO RELATED APPLICATIONS

This application is a non-provisional application that claims the benefit of U.S. Provisional Patent Application Ser. No 61/498,576, filed Jun. 19, 2011 to Hanina et al., titled APPARATUS AND METHOD FOR RECOGNITION OF PATIENT ACTIVITIES, the entire contents thereof being incorporated herein by reference. This application is also a Continuation in Part Application of U.S. patent application Ser. No. 12/815,037, filed Jun. 14, 2010 to Hanina et al., titled APPARATUS AND METHOD FOR RECOGNITION OF PATIENT ACTIVITIES WHEN OBTAINING PROTOCOL ADHERENCE DATA, which claims the benefit of U.S. Provisional Patent Application Ser. No. 61/331,872 filed May 6, 2010, to Hanina et al., titled APPARATUS AND METHOD FOR RECOGNITION OF PATIENT ACTIVITIES WHEN OBTAINING PROTOCOL ADHERENCE DATA, the entire contents of each of these applications being incorporated herein by reference.

FIELD OF THE INVENTION

This invention relates generally to patient compliance in medication administration protocol scenarios, and more particularly to an apparatus and method for the collection, analysis and transmission of data related to patient movements related to such medication administration in order to improve adherence with prescribed drug protocols in accordance therewith. The invention further relates to a tracking and guidance training system for individuals taking prescribed medication, preferably employing computer vision and activity tracking, and may also provide incentives such as reminding a patient of the benefits of a particular medication, providing the patient monetary points or other remuneration on the screen, and one or more reminders to take an appropriate medication. The invention finally preferably relates to the use of computer vision and activity recognition for determination of proper administration of injectable, inhaler-based, or other non-pill medication administration in which proper position and action sequence is important, but is equally applicable to pill based medication administration sequences.

BACKGROUND OF THE INVENTION

Dr Lars Osterberg, M.D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series,* 2008 *Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication. As has been shown in regards to various public health medication administration situation, such as administration of tuberculosis medication by the WHO, Directly Observed Treatment (DOT) improves compliance of patients. *Global Tuberculosis Control: A Short Update to the* 2009 *Report*, World Health Organization, 2009. As is shown in this report, funding for implementing DOT programs is high. Thus, the ability to implement such a program with less of a financial burden would be desirable.

Traditionally, participants attend introductions and follow ups for clinical trials in-person. Other patients outside of the clinical trial setting attempting to adhere to a particular medication protocol similarly are given a prescription and a particular set of instructions from a prescribing medical provider or prescribing doctor, and then compliance is measured at a next visit with that prescribing professional through traditional methods of counting unused medication, and patient interviews. Thus, data collection is similarly limited to patient visits, rather than on a daily basis. These old methods such as patient questioning and medication counting have been proven to be inadequate measures of adherence and offer no information on dose timing and drug holidays (omission of medication for three or more sequential days).

Compliance technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times. Additionally, none of these techniques allow for the monitoring of non-pill related medications, such as the user of inhalers or injectable medication. These medication delivery systems require additional monitoring, as know when administration took place is not sufficient. Rather, positioning and other technique issues may substantially affect the proper delivery and efficacy of particular medications.

Jo Carol et al. stated that "The most reliable method for research purposes, although not practical in a clinical setting, may be a combination approach that includes pill counts, patient self-report, and electronic monitoring." (Carol J. et al, Patterns to Antiretroviral Medication, The Value of Electronic Monitoring, AIDS, 17 (12), pp1, 763-767, October 2003. To date, technologies alone have only been used to monitor compliance rather than to encourage it. Furthermore, there has been no comprehensive system provided that allows for the management of multiple patients and multiple patient populations. While current technology may allow poor compliers to be recognized, as will be described below, the proposed apparatus and method of the present invention will help to encourage pharmaceutical compliance with non-pill delivered medications, and tackle some of the problems that are encountered in the clinical trial process in particular, and the medication protocol monitoring problem in general.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials and other active patient monitoring of medication adherence.

Most importantly, this system provides no mechanism for actually confirming that a patient is in fact properly administering required medication as required in a clinical drug trial, as prescribed by a prescribing physician in the case where adherence to a particular regimen may prove to be critical to efficacy of the prescription regimen, in various public health scenarios, in situations where failure to keep up a prescription regimen can potentially harm a population as a whole, such as the generation of antibiotic-resistant bacteria strains, in various disease management scenarios, or in home care situations where maintaining proper control of administering healthcare professionals is critical. Further, while the system may be sufficient for one who is in full possession of their mental faculties, any individual who may have difficulty following directions, or one who is actively avoiding medication may still not be taking required medication after it is dispensed. Thus, participants may be forgetful, visually impaired, or otherwise do not believe in the benefit of taking such medication, and may thus not properly log medication administration. Furthermore, as it applies only to pill based oral medication, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Furthermore, this system is expensive and requires constant maintenance to confirm that the various mechanical parts are in working order. Finally, as noted above, the system has no application to non-pill based medications.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant. Similarly, there is no mention of non-pill based medications.

While adherence to medication in general is poor, requirements for use of inhalable medications, such as metered dose inhalers (MDI) and dry inhalers, have an increased burden in that simply confirming actuation of such an inhaler is insufficient. It is important to use inhalers correctly to get the full dosage and benefit from the medicine. By using the MDI correctly, medication has a better chance to reach the small airways, increasing medication effectiveness. Using a good technique can also help reduce the side effects of medications. However, use of proper technique with such inhalers is difficult to instruct and monitor in that between 28% and 68% of patients do not use metered-dose inhalers or powder inhalers well enough to benefit from the prescribed medication, and 39%-67% of nurses, doctors, and respiratory therapists are unable to adequately describe or perform critical steps for using inhalers. Even if patients are able to demonstrate correct technique during consultation with a health professional, they may not maintain this standard at other times. Improvement in patient compliance with therapy will require better doctor-patient communication, improved patient education, the tailoring of therapy to the individual and possible novel strategies such as offering feedback to the patients on further their level of compliance.

Additionally, existing systems fail to maintain an audit trail for post administration review by a medical official or other clinical trial administrator, and further cannot therefore confirm confirmation of proper medication administration or population management.

Therefore, it would be desirable to provide an apparatus that overcomes the drawbacks of the prior art.

SUMMARY OF THE INVENTION

In U.S. patent application Ser. No. 12/620,686, filed Nov. 18, 2009, titled Method and Apparatus for Verification of Medication Administration Adherence; currently pending, U.S. patent application Ser. No. 12/646,383, filed Dec. 23, 2009, titled Method and Apparatus for Verification of Clinical Trial Adherence, currently pending; U.S. patent application Ser. No. 12/646,603, filed Dec. 23, 2009, titled Method and Apparatus for Management of Clinical Trials, currently pending; and U.S. patent application Ser. No. 12/728,721, filed Mar. 22, 2010, titled Apparatus and Method for Collection of Protocol Adherence Data, currently pending, the contents of these four applications being incorporated herein by reference, the inventors of the present invention have proposed a system, method and apparatus that allow for complete control and verification of adherence to a prescribed medication protocol or machine or apparatus use in a clinical trial setting, whether in a health care provider's care, or when self administered in a homecare situation by a patient.

These applications present the only medication management system that may determine whether a user is actually following a protocol, provide additional assistance to a user, starting with instructions, video instructions, and the like, and moving up to contact from a medication administrator if it is determined that the user would need such assistance in any medical adherence situation, including clinical trial settings, home care settings, healthcare administration locations, such as nursing homes, clinics, hospitals and the like, and in clinical trial settings.

The inventive solution, in accordance with one or more embodiments of the invention, may provide a webcam software solution, for distribution by medical professionals to provide a training system for training patients to properly administer their inhalable, injectable, or other non-pill based medication, to automate direct observation of medication administration of inhalable, injectable or other medications, and to provide an audit trail of medication adherence and patient behavior. The inventive system may visually and audibly track medication adherence to inhalable, injectable and other medication during training and actual medication administration in clinical trials or other medication administration scenarios on webcam-enabled laptops, tablets, smartphones and other platforms without real time human supervision. The inventive system may visually and audibly recognize a fixed series of actions, each comprising part of the medication administration process.

In accordance with an embodiment of the present invention, a motion capture procedure for capturing motion information related to the administration of injectable, inhaler-based, or other non-pill based medication, may be utilized in accordance with one or more of the inventions noted in the above-referenced applications. Therefore, in accordance with an embodiment of the present invention, a method and apparatus may be provided for analyzing captured patient motion data, transmitting such captured patient motion data to a remote location (or processing such captured information locally, in whole or in part), receiving information from a remote location (or from a processor maintained locally) and providing information to the patient as preferred in accordance with the present invention.

Further in accordance with an embodiment of the present invention, one or more predetermined motion sequences may be determined and correlated to one or more corresponding medication administration instructions for administration of injectable, inhaler-based, or other non-pill based medication. These predetermined motion sequences may be provided as a number of generic motion sequences, as one or more customized motion sequences, or a combination of both. The group of predetermined motion sequences may comprise a motion language that may be applied to one or more different medication administration sequences, including injectable medication administration, inhaler-based medication administration, other non-pill based medication administration and the like, and other healthcare related processes, such as hand washing or the like, medication administration personnel acting as prescribed or the like, thus allowing for an easy to program generic medication administration sequence, but also allow for customization where appropriate and necessary. These programmed motion sequences may then be applied in accordance with the inventions noted in the applications above.

In yet another embodiment of the invention, one or more methods may be provided for confirming that a user is properly performing one or more of these predetermined motion sequences. Thus, as a user positions themselves or an object before an image capture device, a display may indicate to the user whether the position, distance, and/or skew and angle are correct. If not, the user is preferably provided with indications as to how to correct any one or more of these issues. The motion sequences may include capture of use of an inhaler, injectable device or the like.

In a still further embodiment, one or more audio cues may also be employed. Thus, for example, in the case of an inhaler-based medication, audio monitoring of sound from both the inhaler and patient may be performed and used to further confirm that the patient has in fact properly administered the medication. Therefore, not only may positioning of the inhaler in the correct location and relative angle be confirmed, but activation of one or more inhaler mechanisms, and the inhaling of the medication by the patient upon such activation may also be confirmed. Similar monitoring may also be performed with injectable and other non-pill based medications.

The system in accordance with one or more of the various embodiments of the present invention may also be applicable to training situations where the user is provided with various feedback instructions related to training to properly administer medication in a clinical trial or other disease management scenario. In accordance with various embodiments of the present invention, for example, when applied to an inhaler, a patient may be requested to shake the inhaler before use. When applied to an injectable medication, the patient may be requested to confirm refrigeration or confirm proper sanitization of an injectable tip with an alcohol swab or the like, confirm that the needle is not bent, or that an injectable solution or medication has not changed color, or otherwise become spoiled in a manner that is visually detectable. While online training and instructions may be available currently, the interactive nature providing feedback to the user regarding their use and following of protocol is critical in improving adherence and patient action.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 1:
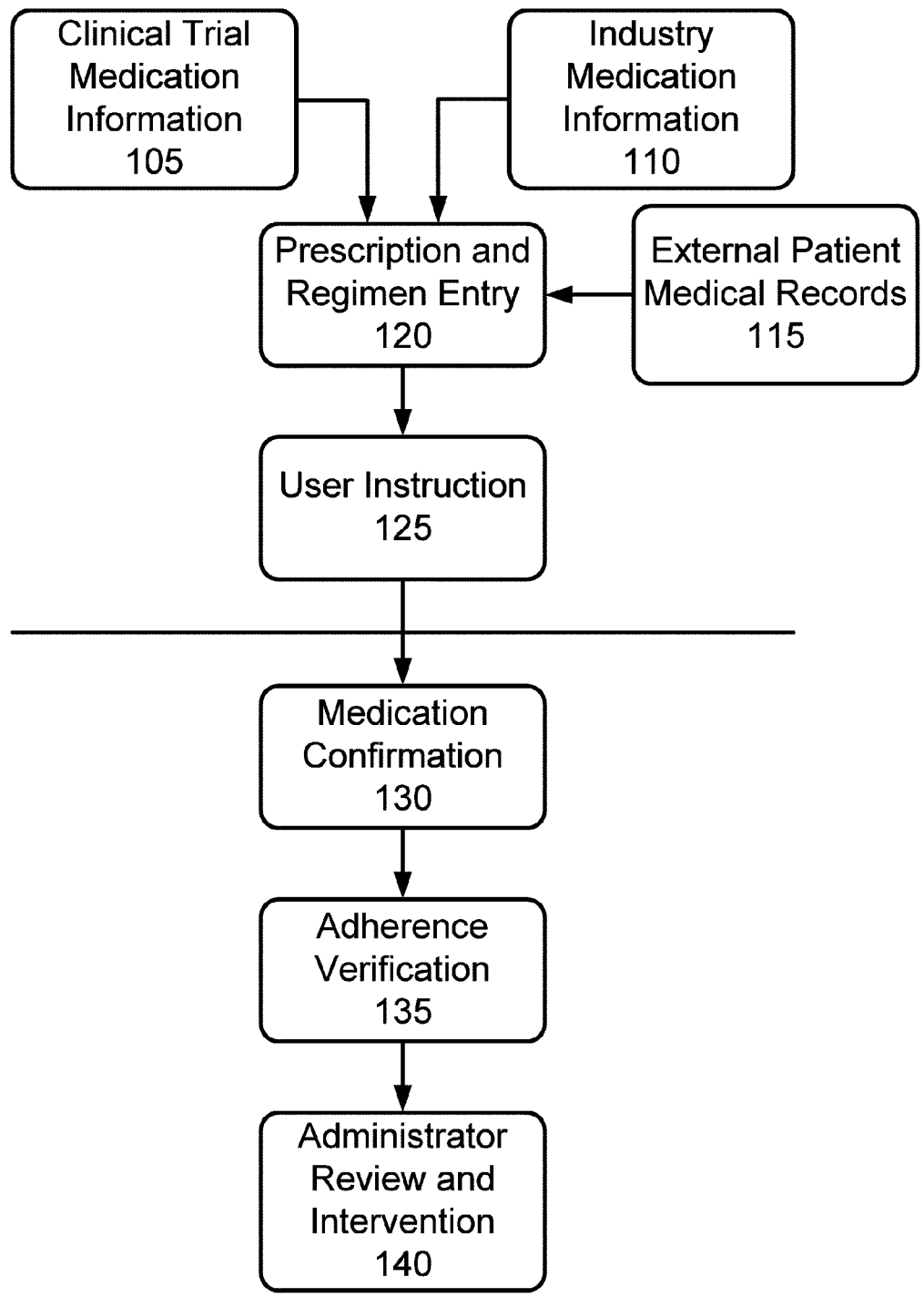
FIG. 1 is a flow chart diagram depicting a method in accordance with an embodiment of the invention.

The invention will now be described making reference to the following drawings in which like reference numbers denote like structure or steps. Referring to FIG. 1, a data flow overview in accordance with the operation of an embodiment of the present invention is shown. In accordance with this embodiment of the invention, information about a particular drug to be the subject of a clinical trial, to be employed in a public health or disease management situation, or the like, or other medication administration program or prescription may be provided in a database 105, and existing industry medication information databases 110 are preferably employed to access prescription, interaction, application, and other available information about any number of proposed prescription and non-prescription medications and their possible interaction with the clinical trial or other medications. Further, patient medical records 115 may be used, and as will be described below, are used in conjunction with the industry medical information and a medical professional's prescribing expertise to confirm that a patient is a good candidate for such a clinical trial, or medication administration program. These databases may be accessed in a manner known to one of ordinary skill in the art.

Once confirmed, a medication administration regimen in accordance with the clinical trial or other prescription requirements such as in a public health, medical practice environment or the like may be prescribed and entered into the system of the invention at 120. Once entered into the system, a particular prescription regimen may cause a set of user instructions, various training sequences and the like 125 to be generated and transmitted to an apparatus provided to a patient in accordance with an embodiment of the invention for access to the system of the invention. Such an apparatus may comprise a custom designed video and audio capture, analysis and transmission apparatus, a smart phone or other mobile device including a camera or other video and audio capture apparatuses, a netbook, laptop computer, desktop computer, tablet device or the like, or other computing appliance allowing for the display of instructions to a patient, and allowing for the eventual capture, analysis and transmission of video, audio and other analysis information. When installing software on a user's own hardware system, it is preferred that the software detect and otherwise test or determine that the hardware attempting to be utilized by the patient is sufficient to implement the invention and is sufficient to run a software package provided in accordance with the invention. Thus, the software may check that a camera includes sufficient resolution, that a memory of the device is of sufficient size to allow for sufficient captured video storage, that audio may be properly captured, and that the transmission system includes sufficient bandwidth to transmit and receive captured video, audio, video instructions and the like.

In a clinical trial or other administration settings, patient instructions and various training sequences may be varied for different users to determine the best set of instructions, or may be varied based upon demographics, experience, or other factors that may require different types of instructions to be provided. It is further contemplated in accordance with an embodiment of the invention that multiple clinical trials or patient populations may be managed by a manager in accordance with the invention so that the invention contemplates a medication administration system that allows for a single point of management for all clinical trials or patient management groups associated with a particular manager or the like. Such management techniques in accordance with the embodiment of the invention may further be applied to various public health situations, disease management scenarios and the like.

Such user instructions and training sequences may include general instructions about the particular medication subject to the current trial or medication administration protocol, methods for administration, warnings about side effects, and concerns about drug interactions with common substances or medications, or other medications prescribed to the patient by the system or by another medical service provider. It is contemplated in accordance with an embodiment of the invention that such set of user instructions may be interactive, allowing a user to view additional information about such instructions or prescriptions as desired. These instructions may comprise written, audio or video instructions provided to the user on a display of the user apparatus. It is further contemplated that such instructions may indicate one or more movement sequences to be associated with a corresponding one or more medication administration sequences. A more in-depth description of the information provided at step 125 is depicted in FIG. 2.

Figure 2:
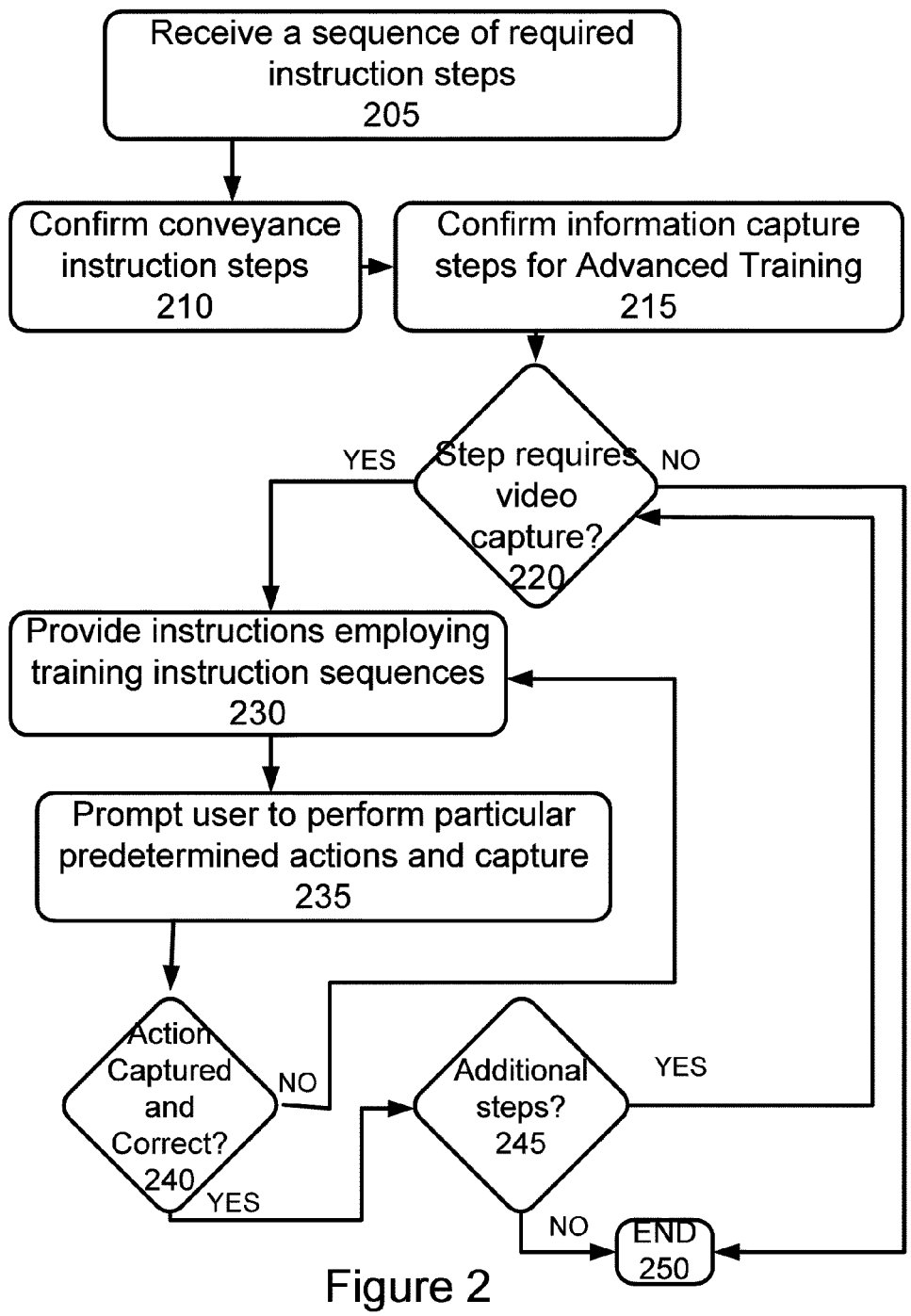
FIG. 2 is a flowchart diagram depicting a video sequence generation method in accordance with an embodiment of the invention.

As is shown in FIG. 2, the generation and provision of user instructions as set forth in step 125 first comprises the step of receiving a sequence of required instruction steps at step 205. This sequence may be determined as described above in step 120. The system then may confirm whether one or more of the instructions steps require the conveyance of information to a patient at step 210. These conveyance steps may comprise a more conventional instruction step, such as the display of written information, comprise a more advanced instruction step, such as the conveyance of audible information, video instructions or the like, or may comprise an interactive instruction step, such as an interactive instruction sequence displaying a desired sequence of information to a patient, and then monitoring and confirming whether the patent has properly administered the medication. Various feedback mechanisms may be provided to allow the patient to try multiple times to perform proper administration, and may also provide varying encouragement or instructions to confirm that administration training has been performed properly. Thus, such an instruction and training sequence may include the eventual capture of video, audio and other information from the user. Therefore, at step 215, it may be determined whether one or more of the instruction steps will require the capture of information from the user, thus comprising an advanced interactive training sequence. Thereafter, each of the training steps requiring capture of video information from a user is confirmed at step 220. If no further video capture is required, and therefore various training or other interactive sequences have been completed, processing for step 125 then ends at step 250. If it is determined that the capture of video and/or audio information will be required at step 220 for the current training step, then processing passes to step 230, and various instructional video, audio and other sequences may be provided to the user in an instructional sequence format.

After being shown a particular instructional sequence, preferably applicable to a particular step of a medication administration protocol sequence, then processing passes to step 235 where the user may be prompted to perform a particular action or sequence of movements. The user may request to be re-shown these sequences as many times as necessary, and may also include audio or other instructions, so that the user is provided with a training sequence, thereby reducing variability of future performance of that action. When preparing to perform these actions, an alert system may be employed to warn the patient of any issues that may interfere with the proper capture of video and/or audio information, as may take place similarly when actually administering the medication. Thus, the user may be encouraged to properly perform these sequences, thus acting as an interactive training module.

Figure 4:
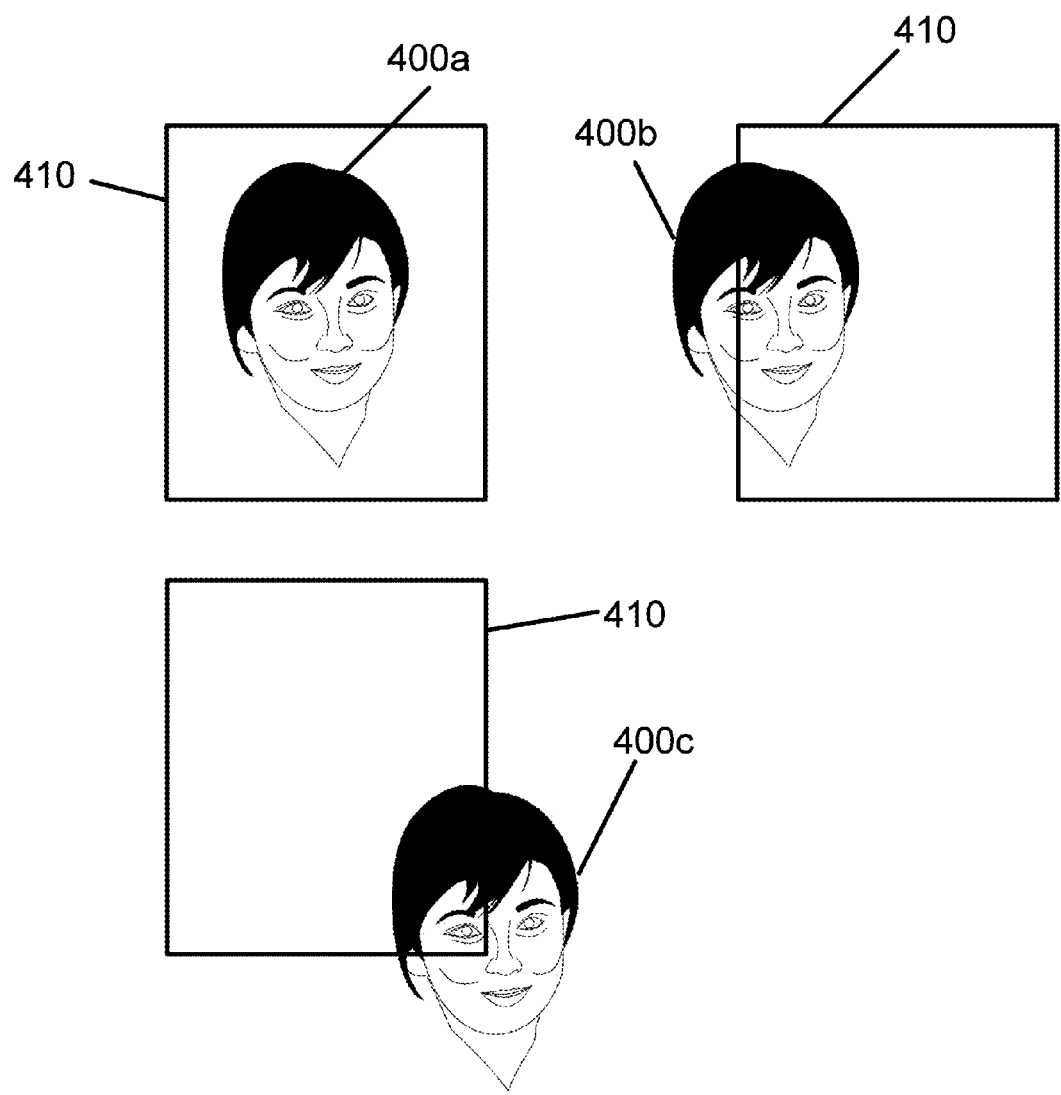
FIG. 4 is a depiction of a positioning process in accordance with an embodiment.

Thus, the user may be notified if they are sitting in a manner in which their actions cannot be properly captured, if they are blocked from the camera, the light conditions are insufficient, if an object they are holding is in an improper location, or the like. As is shown in FIG. 4, a box 410 may be provided on a display viewable by a patient using the system. A representation of the patient's face may be shown in a position relative to an optimal filming position for the use of, for example, an inhaler for medication administration. Thus, while facial representation 400a is properly positioned, facial representation 400b is positioned to the left of the box, while facial representation 400c is positioned down and to the right of the box. A similar positioning system may be provided for an injectable medication, the position of a patient body part being provided in place of the facial positioning described above. Thus, not only may proper positioning be determined, but use of the proper body part may also be confirmed. In practice, the box may be made a red or other warning color until proper alignment is achieved (including if a user or desired user body part is not positioned fully within a screen, the user is too close or far from the camera, or for any other reason), at which time the box may change to green or other appropriate color. Further, audio clues may also be given to the patient, such as increasing frequency beeping as the optimal position is approached. Thus, in accordance with an embodiment of the present invention to be employed for inhaler medications, the user is provided with immediate feedback on their position and the ability of their actions to be properly recorded and analyzed. As the user interacts with the system of this embodiment of the invention, such a scheme may be employed to provide continuous feedback to the user, and thus indicating whether the system is able to properly capture and/pr analyze the actions of the user. If time is passed and the user is unable to properly position themselves, or to properly perform desired actions, additional guidance may be provided to the user in order to remedy such a situation, including but not limited to directional indications, voice commands, video images of proper technique, etc.

Figure 5:
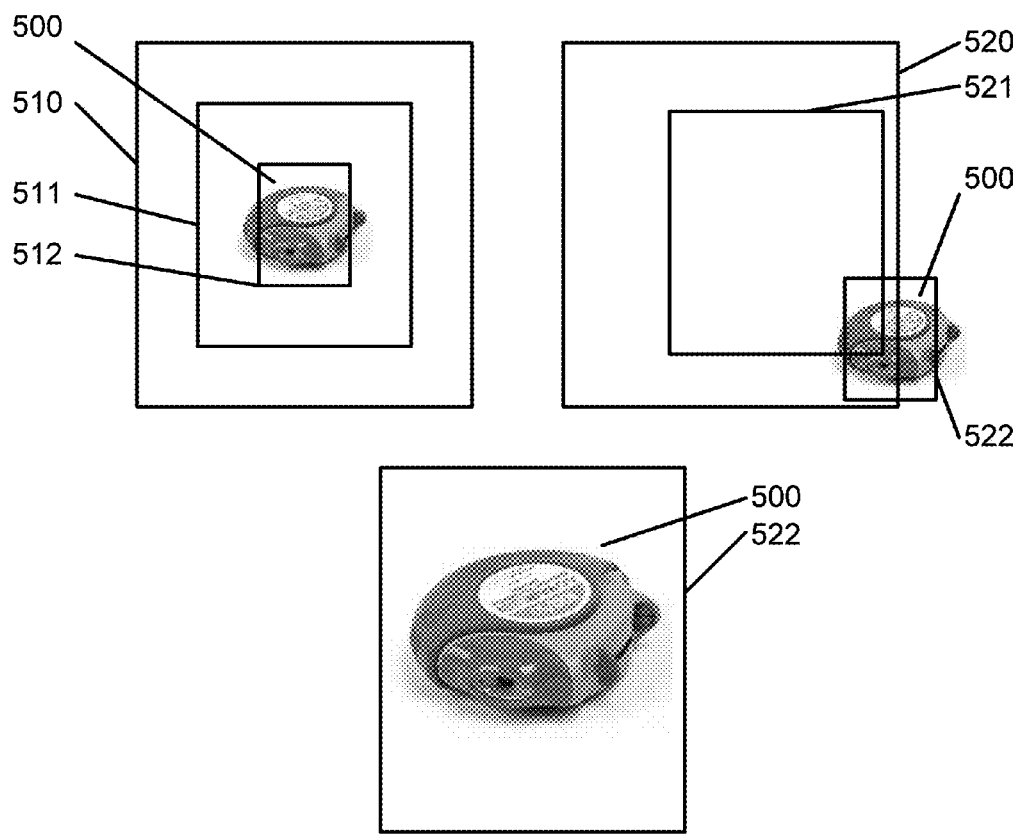
FIG. 5 is a depiction of another positioning process in accordance with an embodiment of the invention.

In addition to properly positioning the patient, proper positioning of one or more objects, either absolutely or relative to another body part, may be determined, such as positioning an inhaler relative to the mouth and face of the user, an injectable medication delivery device relative to the body part of the user to receive the injection, or the like for imaging and processing in accordance with an embodiment of the invention. As is shown in FIG. 5, an inhaler 500 may be indicated as properly positioned by a box 522, the box being green, for example, as in the description of FIG. 4. Such an object, however, is more likely to be improperly positioned not only left to right and up to down, but also in distance to the imaging apparatus, in accordance with one or more limitations of the imaging device, such as the resolution thereof, low light positions, and the like, and any affect such resolution might have on the ability of the imaging device to identify shape, color text or other coding, or the like associated with the object being imaged. Thus, if positioned too far away from the imaging apparatus, a sequence of boxes 510, 511, 512 and a small representation of inhaler 500 may be provided to alert the user to move the inhaler closer. If the inhaler is not only too far away, but off center, boxes 520, 521, 522 may be provided to guide the user to move the inhaler into proper position absolutely and relative to the mouth and face of the user. Similar functionality may be provided for positioning an injectable apparatus relative to a user body part to receive the injection, including relative angle and distance to the body part. By properly positioning such a device, the system may be employed to confirm the identity of such a medication, employing shape, color, labeling, and the like. In addition to determining identity of the medication, such processing may be used to determine safety of the apparatus, such as whether an inhaler or injectable device may have been damaged or tampered with. Further, the medication may be observed to determine any change in color or other characteristic of the medication that may suggest spoilage, improper medication, counterfeit medication or the like. The apparatus, in accordance with an embodiment of the invention, may thus ask the user to move the inhaler or injectable device closer to or further away from the imaging apparatus, may change an ambient light sensitivity of the apparatus, or may otherwise change details of the image capture. As noted above, both color and audio prompting may be provided.

Figure 6:
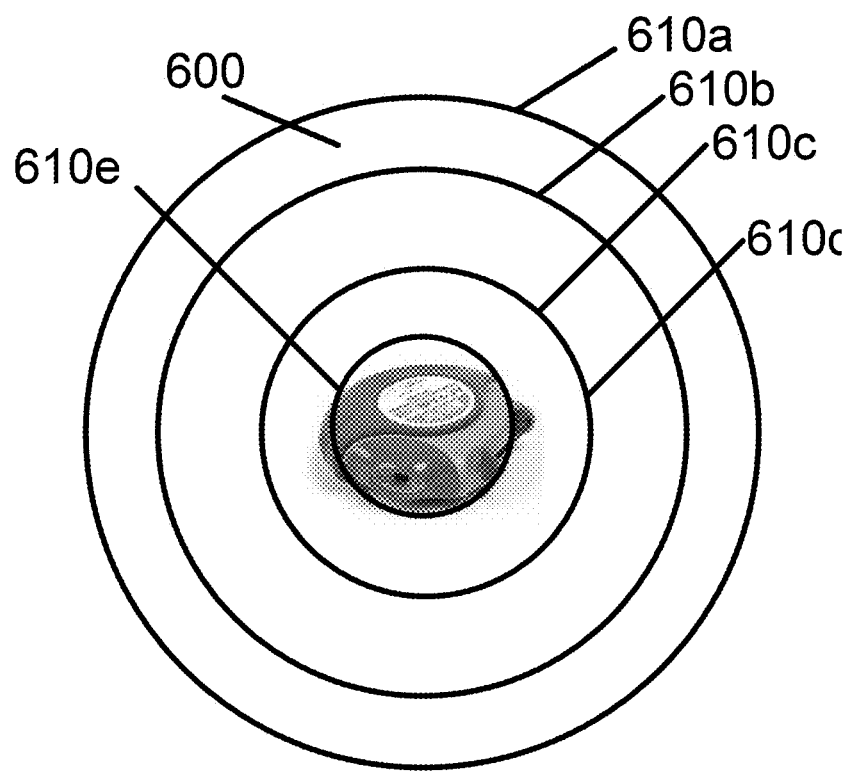
FIG. 6 is a depiction of yet another positioning process in accordance with an embodiment of the invention.

To the extent that positioning and orientation of the inhaler, injectable medication administrator or the like when being used is important, a similar system may be employed. As is shown in FIG. 6, a set of concentric circles 610a-e may be provided to aid in the positioning of an inhaler 600. A center circle 610e may be provided with a solid center (not shown) upon proper placement of the inhaler. These circles may move as the boxes in FIG. 5, and may further use color and/or audio prompts to instruct the user. Further, as images of inhaler positions and orientations, or inhaler and hand positions and orientations, are to be captured and analyzed, the system may also preferably indicate not only proper positioning, but actual acquisition of a correct position and orientation sequence. In accordance with an additional embodiment of the invention, such recognizable positioning and orientation may further comprise a sequence of gestures and apparatus movement and orientation employed to ensure that the patient properly administers their medication. In accordance with an administration process, as noted above, the patient may first be trained to show a particular medication administration device or apparatus in their hand to the camera for imaging and recognition. The patient may then be asked to place the apparatus at an appropriate administration location, such as against the mouth in the case of an inhaler apparatus, or at a particular body part location in the case of an injectable medication. Thereafter, actuation of the apparatus, through the process of monitoring movement and audible cues may be employed. Thus, through a predetermined sequence of actions that are captured, imaged and analyzed, evidence of proper administration can be recorded and analyzed.

Furthermore, in accordance with one or more embodiments of the invention, various additional aspects of medication and/or administration may be checked and confirmed. Thus, the system may employ such computer vision and activity recognition to determine a liquid color, liquid consistency or clarity, potential existence of particles, perhaps suggesting a spoiled medication, bubbles in the liquid, suggesting improper handling, in an injectable administration system. Through the use of the system, a number of administrations can be tracked, and a liquid or other level may be used to confirm the count, thus potentially allowing for the addition ordering of further medication, or other counting of inhaler administrations without the need for expensive inhaler units. Also, dosage settings, if applicable on an injectable pen or other apparatus may also be confirmed before administration.

Figure 7:
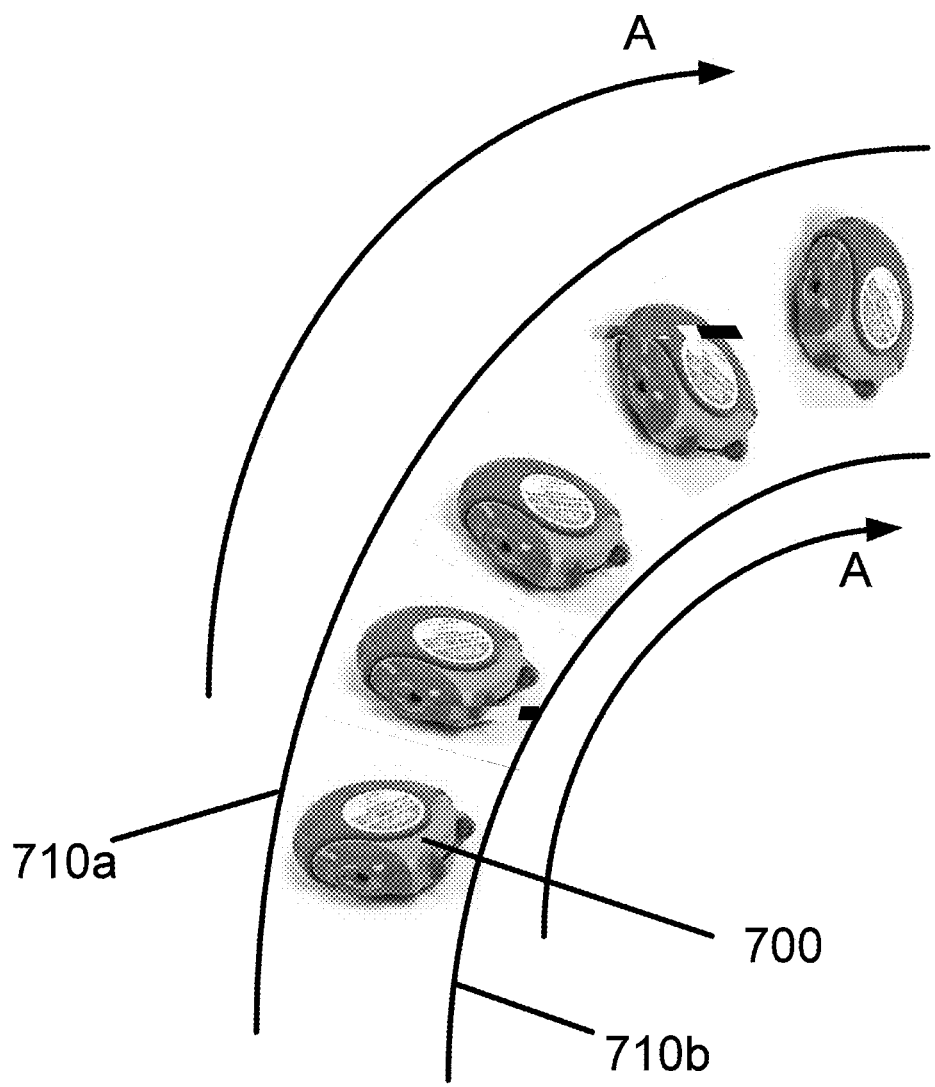
FIG. 7 is a depiction of a motion tracking process in accordance with an embodiment of the invention.

Furthermore, as is shown in FIG. 7, when tracking the movement of a medication administration apparatus 700, it is preferable to depict to a patient whether they are holding the apparatus at a correct orientation, when the apparatus is in transit, or positioned at the administration sight. Thus, as is show in FIG. 7, an administration apparatus 700 is indicated to be reoriented from a horizontal to a vertical orientation through movement in the direction noted by arrows A. A set of guidance tracks 710a, 710b may be displayed to a patient and successive apparatus positions and orientations may be superimposed thereon. As the apparatus moves along the proscribed path, concentric circles such as those depicted in FIG. 6 may be employed to confirm proper location and orientation. Thus, in accordance with an embodiment of the invention, a virtual path may be shown to the user to ensure that the proper method of medication administration is followed. As noted above, color and/or audio sequences may also be employed. Similar positioning information may be processed relative to an injectable medication.

Therefore, in accordance with one or more of the positioning assistance schemes noted in FIGS. 4-7, a patient may be guided to properly present themselves or an object to an image capture device for capture and interpretation during the noted training phase, or (as will be described below) during a particular medication administration phase. Any of the display and notification techniques noted in any of these Figures may be used in any of the other Figures, in accordance with various embodiments of the invention. Further, these positioning techniques may be employed not only during initial training, but during any subsequent system process employing video image capture of people, objects, or any other entity to be imaged, or the use of audio information.

Referring back to FIG. 2, at step 240 these motions of the user may be captured and confirmed as being correct by one or more appropriate computer vision techniques, individual review by a human, or other appropriate determination process. If not correct, processing may return to step 230 to provide the instructions and example sequences again to the user. Therefore, in accordance with the invention, repeated instruction may be provided to the patient until training can be confirmed that the patient has performed the desired sequence correctly, thereby aiding in limiting future variability in the actions taken by the patient during administration. Such instruction may take the form of analysis of a recorded user action, and comments on what the user may be doing wrong, and how this action may be improved. Once the user has received sufficient instruction, and it is therefore determined that the user has performed the action in a manner that is sufficiently similar to the instruction set, and substantially consistent over a number of performances of the action, processing then passes to step 245 where it is determined whether there are additional training steps to be presented, and therefore additional video sequences to be captured. If so, processing returns to step 220 for further processing. If not, processing ends at step 250.

Referring back to the lower portion of FIG. 1, the horizontal line indicates a time for patient administration of medication. At such time, the user may be notified to take their medication through any desirable communication and notification system, including text messaging, email, telephone call, automated calendar reminder or the like. While not explicitly shown, first, preferably the identity of a user is confirmed through the use of a facial recognition sequence, other biometric identification sequence, or other password identification system. Upon recognition of the individual, the system may display one or more data regarding the individual, such as, by way of example only, name, patient status, medication to be administered, calendar indicating to the patient when medication has been administered and if any administration times have been missed, and, selectively, a score indicative of a level of compliance of the individual with the medication protocol, if desired. Once identified and notified of a type of medication to be administered, the patient may display a medication administration apparatus, such as an inhaler, injectable apparatus, or other medication form (including a pill bottle, pill, or the like) to confirm that the medication is correct and is the currently prescribed medication to be taken through the use of text recognition, medication recognition, barcode or other code reading of one or more unique identifiers from the administration apparatus, pill bottle or the like, or other appropriate medication recognition scheme. The user may alternatively be shown a virtual medicine cabinet with visual or textual indications of one or more medications to be taken at a particular time. Imaging of one or more of such medication apparatuses may then match a medication apparatus provided by the patient to one or more of the pills in the virtual pill box. Thus, the patient is not only allowed to have a particular medication apparatus imaged, but also may be given a visual representation of medications to be taken, medications that have already been taken, and a visual picture of one or more additional medications to look for if the patient is confused or is not immediately able to locate all of the required medication. Such a display may further act as an additional incentive program for the patient to properly take their medication, and may in turn give a patient other incentives, such as a running score, payment information or other point systems if the patient is to be rewarded for properly taking medication. Thus, credit to buy information from a website or store may be provided. For children, various animations may be provided, and pocket money or other credits may be provided to purchase items online or through one or more stores from supporting merchants may be provided. The display of such information may assist in convincing the patient to continue to properly take medication. This sequence of steps therefore acts as an audit trail each time a medication is taken, that can be reviewed later, to ensure that a patient is properly following a regimen. Any of the positioning schemes depicted in FIGS. 4-7 may be employed.

Additionally, after confirmation or failure of confirmation of such administration, the user may be provided with a progress report regarding how they have performed over time, and further providing encouragement for future adherence. Additionally, notice of a next administration time may be provided, along with one or more messages from a healthcare provider regarding protocol changes, or other desired information.

Furthermore, use of a combination of visual and/or audio cues may be employed to further determine sequence and timing. Thus, not only should an inhaler be properly positioned, for example, but during use, an inhalation by the patient should occur immediately after actuation of the inhaler. Thus, by visually and/or audibly confirming first actuation, and then inhalation, this sequence of actions can be confirmed. Sound and visual signatures related to each of these actions may be employed to improve a confidence with which the system is able to confirm proper administration. Similarly, an injectable may need to be properly positioned and maintained in a particular position after administration, such as maintenance of a needle after actuation of the injection mechanism for a predetermined period of time.

In accordance with the invention, confirmation of patient adherence to the prescribed administration schedule for the medication as prescribed by the clinical trial or other prescription regimen may be determined. While such confirmation may take a number of forms, in accordance with the invention, a preferred method for such confirmation may include capturing a video and audio sequence of the patient actually administering the medication. In a further preferred method, such a sequence for such confirmation may include employing a facial recognition sequence or other biometric confirmation that a particular patient is in fact receiving treatment, but may also provide for the ability to obscure the face or other identifying feature of a user, or otherwise encrypt such information to allow for the storage and use of such images while protecting the identity of the patient, a technique that may be beneficial when a medication administration manager is providing a general report about a clinical trial, and not trying to remedy a situation with a particular patient, or in particular in a public health or disease management scenario. Activity recognition, gesture recognition or other feature for determining whether a particular subject movement meets a predefined movement sequence may be employed to be sure that the patient is properly taking prescribed medication.

Figure 3:
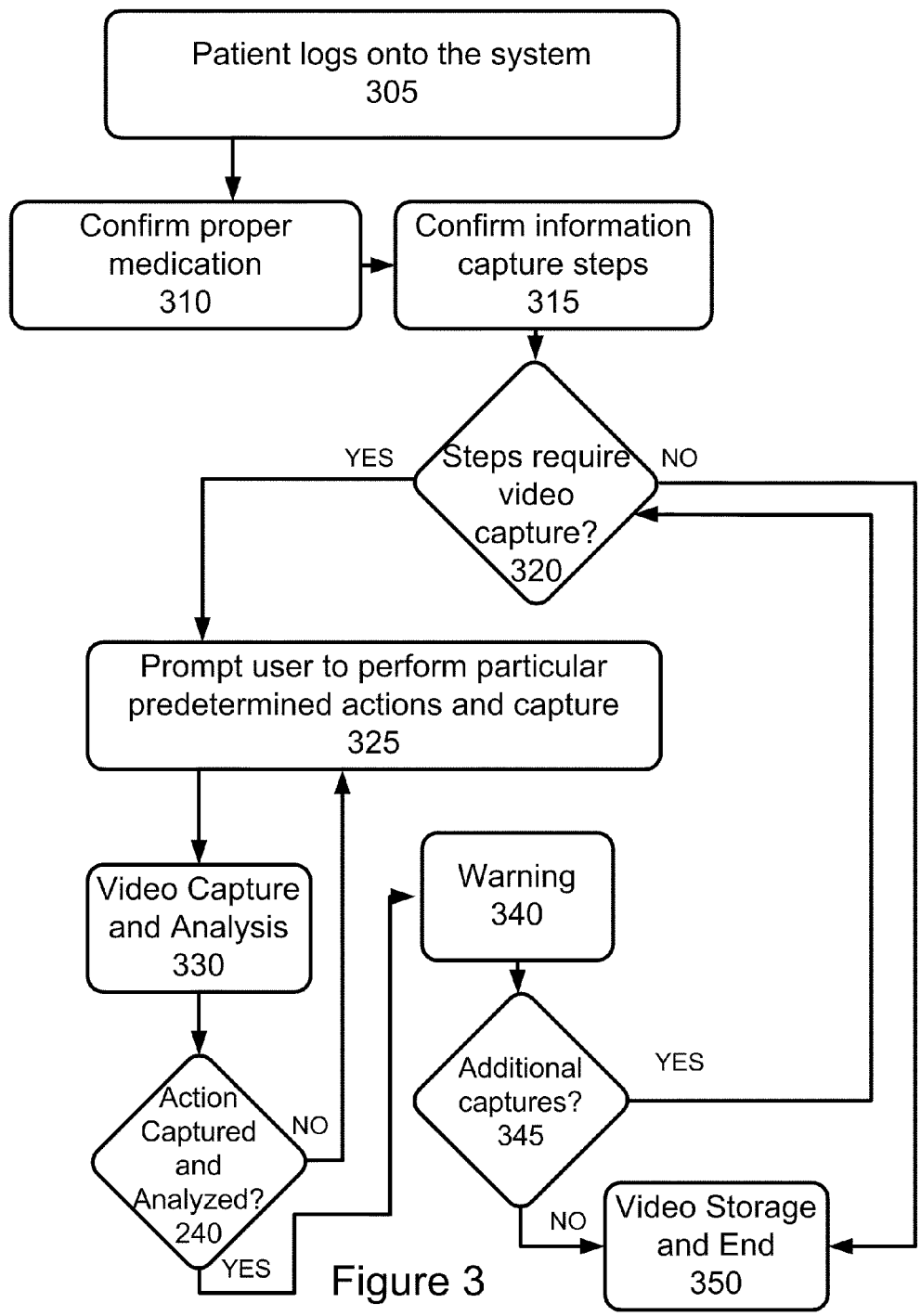
FIG. 3 is a flowchart diagram depicting a video sequence capture method in accordance with an embodiment of the invention.

Referring next to FIG. 3, a method in accordance with an additional embodiment of the present invention for performing audio and video capture and recognition of adherence to a prescribed protocol is described, as set forth in steps 130 and 135 of FIG. 1. In FIG. 3, a patient may first log into the system of the invention at step 305, employing the facial recognition, biometric recognition, password entry, or other patient identification method, and at step 310 proper medication is confirmed as noted above, through the user of bar code reading, text recognition, visual recognition employing video or still image recognition, or other medication recognition technique. The patient may be reminded to log onto the system to take their medication through any type of reminder, such as a text message, email, phone call, automated alarm or the like. Of course, any of the positioning techniques previously described in reference to FIGS. 4-7 may be employed. Next, at step 315 it may be confirmed that the process involved will include one or more information capture steps, and at step 320 it may be determined whether these information steps will include video capture. If not, video processing ends after storage of any non-video information. (Alternatively, steps 315 and 320 may be excluded if it is determined that each confirmation sequence may employ video capture, then video processing may pass directly to step 325, as described below.) If it is confirmed at step 320 that one or more steps will include video and/or audio capture, processing then passes to step 325 where the user may be prompted to perform one or more predetermined actions, these actions being captured. Positioning of the inhaler, injectable medication apparatus, or other medication may be performed in accordance with any of the techniques as described previously in reference to FIGS. 4-7. Such recognition in the case of an injectable administration apparatus may also comprise confirming relationship of the injectable administration apparatus and a prescribed body part, proper actuation of the administration apparatus, maintaining the administration apparatus in the location for a predetermined period of time, and perhaps proper post administration action, such as cleaning and storing the apparatus, refrigerating the apparatus, cleaning an injection site and the like. Further, voice recognition may be utilized to allow the user to enter commands, and an audio output may be provided for aiding the user in properly adhering to instructions from the system. Additional audio cues may be recognized, such as upon visual confirmation of administration of an injectable or inhalable medication, audio signatures may be employed in order to determine whether insufficient pressure may have been used, or whether a sufficient or extensive period of time has passed from actuation to inhalation. Proper capture of patient actions is very important as the patient only administers the medication once per capture period.

Video capture analysis may then begin at step 330, such analysis comprising analysis of the newly captured video and/or audio, as provided as noted above with respect to FIG. 2. At step 335 it may be determined whether the action has been properly captured, and whether the captured action has been properly analyzed by the system. Various incentives may be provided to the patient to encourage them to take their medication properly. Thus, in addition to providing various reminders to a patient as is known in the art, points, monetary or other incentive may be provided to the user for actually having medication administration confirmed. Further proper administration with less errors, etc. may be rewarded more highly, thus giving incentive for the patient to concentrate on administration issues and to attempt to have such administration be as accurate and consistent as possible. Such incentives and medication tracking may be used to determine future courses of treatment or payment. For example, if a patient consistently fails to take medication as required, perhaps a different course of treatment requiring fewer medication administrations may be better for this patient. Alternatively, if a medication requires a consistent administration and is very expensive, failure to comply with administration instructions may be cause for an insurance company, prescribing doctor or the like to not renew such a prescription for the patient, thus saving money in a situation where the money was being wasted because of lack of compliance.

If it is determined that administration of the medication did not take place properly, processing may return to step 325 and the user may be once again prompted to perform the action. Of course, if this process involves actual administration of inhaler or injectable medication, it may not be proper to request re-performance of the action, unless it can be determined that the user did not actually administer the medication. If the action has been properly captured, and is able to be analyzed, processing passes to step 345 where it may be determined whether additional captures are required. If so, processing returns to step 320. If no further captures are required, processing ends at step 350 where the various captured video sequences are stored. These stored sequences may also be made available for human review and involvement, when it is determined that this would be beneficial.

Therefore, in accordance with various embodiments of the invention, because a video image of the patient actually administering an inhalable or other medication (or other method of medication administration, including but not limited to injections, dialysis, and any other medication administration procedure) may be captured and analyzed, actual confirmation may be achieved, rather than simply relying on the patient to state that a particular medication was administered. Such a video image may be captured or stored in any appropriate format given a selected type of activity or gesture recognition that is employed in accordance with a particular embodiment of the invention. Such may include full video, biometric data points, recording of movement of an article, such as a bracelet or the like, affixed to the patient or administrator, use of mapping to provide a stick figure or other body movement tracking technique, or gesture or activity recognition to determine movement or the like. The user may be encouraged to use a particular sequence of movement to be confirmed that they are properly administering the medication according to the protocol, thus reducing the possibility of the potential appropriate movements considered to be "correct." Or, as noted above, capture of customized video sequences may be performed so that the user is more likely to repeat these same actions. Indeed, various instructional videos or other appropriate training may be provided to a user to insure they properly administer the medication.

This captured adherence information may be provided to a healthcare provider, clinical trial manager or the like through a dashboard allowing for the review of information about an individual patient, entire population of patients, or demographically relevant information. Such information may be provided to easily notify the healthcare provider, clinical trial manager or the like of problem patients, demographic groups, medications or the like. One or more dashboards or other reporting mechanisms may be employed as described in copending U.S. patent application Ser. No. 13/189,518, filed Jul. 24, 2011 to Hanina et al., titled "Method and Apparatus for Monitoring Medication Adherence", the entire contents thereof being incorporated herein by reference. Thus, any adherence or other information obtained in accordance with the present invention may be provided to one or more individuals in accordance with one or more methods or systems as described in the '518 application.

Through the use of training as described above, a type of administration language may be generated, allowing for extension to other patients, and also allowing for interpretation of reason for differences from a predefined sequence by a patient. Thus, if a patient performs an action differently over time, this difference may provide insight to a reaction to a medication, changes in the patient's medical condition, or the like. It is further anticipated that analysis of large numbers of patients will allow for a more flexible system that may recognize more of a patient's movements, and thus may improve the ability of the system to function properly.

Therefore, in accordance with an embodiment of the invention, a user may perform a predetermined sequence of actions designed to ensure performance of medication administration. Thus, by way of example only, for an inhaled medication as noted above, the user may be asked to first show a medication and may then be prompted to position the medication administration apparatus relative to their mouth in a desired manner. Next the user may be prompted to administer the medication, the action of administration being captured on video and audio, and being interpreted to confirm that the medication has been properly administered. Of course, in accordance with this embodiment of the invention, other action sequences may be employed, and may be mixed with other actions to be performed by a patient or caregiver. Thus, but defining a medication adherence protocol as a single or sequence of gestures that may be recognized by a processing system, the accuracy of confirming that a patient has actually taken a particular medication is improved. Through an interactive learning process, the processing system may also learn patient behaviors to be more accurately determine medication adherence, and to remove some of the potential false positives or false negatives. If a caregiver is involved, it is contemplated that the caregiver be provided with a number of gestures indicative of particular actions to be taken, and use of these gestures prompting the system to confirm that these actions are in fact being taken. Thus, a full audit trail of not only the patient, but also the caregiver may be determine, such as whether they approached the patient at the correct times, or that they washed their hands when approaching.

Further uses of the video capture sequences may also be employed, including video capture of responses to questionnaires about current patient states of discomfort, informed consent, example of questions to be asked, video transmission of such questions and the like. The patient may be able to send a video message, pointing to a particular pain or the like, and may include an audio portion as well. Time stamp markers may also be captured to confirm that the user is taking their medication at appropriate times and a number of times a user has taken a particular medication, to confirm whether there are substantial delays between instruction and administration, or for any other time sequence determination. Furthermore, other behavioral markers, such as, by way of example only, shaking hands indicating a particular ailment, or other movements by a patient that may give a hint as to the physical or mental status thereof Additionally, if the user is taking medication that is improper, or they have already taken, a warning may be provided to warn the user to stop medication administration immediately.

In accordance with various embodiments of the invention, when considering administration of an inhalable or injectable medication, analysis of adherence video sequences may be employed to determine a likelihood that a patient has actually administered their medication. Thus, based upon video and audio cues determined related to positioning and use of the medication administration apparatus, it may be determined that the patient is having problems properly positioning the apparatus, and therefore the system is unsure that the patient has administered the medication properly. Low confidence in proper administration based upon failure to properly position the apparatus, failure to record audio signals indicative of proper administration or the like may be employed to determine whether a patient should be retrained, via the automated training system described herein, by automated contact, or by individual personal contact. This determination of low confidence of administration, even if it is ultimately determined that administration likely took place, may still be utilized to determine whether training or other actions may be taken. Such confidence levels may be used, in accordance with a desired algorithm or the like, to provide an overall picture of medication administration by a patients or group of patients, thus allowing for intervention, encouragement, training or the like to be provided when it appears that actions are changing, but not necessarily waiting until a critical issue is discovered.

It is further contemplated that the method and apparatus of the invention allow for integration with one or more audio or video conferencing systems, thus receiving and/or providing information there through. Thus, a user may employ a standard video conferencing tool or system, and have this information be coupled to a mobile or other device being used in accordance with an embodiment of the present invention.

Therefore, in accordance with the invention, a method and apparatus are provided that allow for the automated confirmation of adherence to administration protocol for medication, and provide for a most sophisticated method for confirming and studying methods of administration of such prescription medication.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A medication administration confirmation apparatus, comprising:
    a display associated with a local device for displaying audio-video instructions for instructing a user to properly administer a medication in accordance with a sequence of interactive instruction steps indicative of proper medication administration employing a medication administration apparatus, at least one of the audio-video instructions instructing the user to follow one or more of the sequence of interactive instruction steps to properly position the medication administration apparatus relative to a user of the medication administration apparatus;
    an audio-video capture device associated with the local device for capturing one or more audio-video sequences of the user administering medication following a display of one or more audio-video instructions encouraging adherence to the sequence of interactive instruction steps encouraging properly positioning of the medication administration apparatus for proper medication administration;
    a memory for storing on the local device the captured one or more audio-video sequences; and
    a processor operable to perform operations on the local device for providing a user real time feedback during medication administration on how to properly administer medication and position the object associated with proper medication administration as the user positions the object before the video capture device, wherein the operations comprise:
        outputting to the display one or more audio-video instructions for instructing a user to properly administer medication in accordance with the sequence of interactive instruction steps indicative of proper medication administration employing the medication administration apparatus, at least one of the audio-video instructions instructing the user to properly position the medication administration apparatus associated with medication administration,
        receiving, from the audio-video capture device, one or more audio-video sequences of the user administering medication following the displayed one or more audio-video instructions encouraging proper medication administration in accordance with the sequence of interactive instruction steps, including at least properly positioning of the medication administration apparatus associated with medication administration, and
        in response to receiving the one or more audio-video sequences, automatically analyzing in real time motion of the user and/or the medication administration apparatus within at least one of the received audio-video sequences to confirm whether the user has properly administered the medication in accordance with the sequence of interactive instruction steps using the medication administration apparatus;
        determining, from the analysis, that the user has not followed one or more of the steps of the sequence of interactive instruction steps, and that medication has not been properly administered, and
        responsive to determining that the medication has not been properly administered, outputting to the display while the user is administering the medication an additional one or more of the audio-video instructions to the user to encourage following of the one or more steps of the sequence of interactive instruction steps to confirm proper administration of the medication.

2. The medication confirmation apparatus of claim 1, wherein the processor is further operable to output to the display a prompt to the user to perform a particular sequence of actions in response to the displayed audio-video instructions to be stored as the one or more audio-video sequences.

3. The medication confirmation apparatus of claim 2, wherein the particular sequence of actions is designed to assist in determining proper medication administration.

4. The medication confirmation apparatus of claim 1, further comprising a data transmission system operable to transmit one or more of the at least one stored audio-video sequences to a remote location for further analysis.

5. The medication confirmation apparatus of claim 4, further comprising a data reception system operable to receive further information indicative of whether the user has properly administered the medication following the displayed audio-video instructions from the remote location.

6. The medication confirmation apparatus of claim 1, wherein analyzing at least one of the received audio-video sequences comprises confirming proper positioning of an inhalable medication administration apparatus following the displayed audio-video instructions on the display of the local device.

7. The medication confirmation apparatus of claim 1, wherein analyzing at least one of the received audio-video sequences comprises confirming proper positioning of an injectable medication administration apparatus in real time following the displayed audio-video instructions.

8. The medication confirmation apparatus of claim 1, wherein the processor is operable to receive recorded audio of the user administering medication following the displayed audio-video instructions.

9. The medication confirmation apparatus of claim 8, wherein the processor is operable to analyze the recorded audio to aid in determining proper medication administration.

10. The medication confirmation apparatus of claim 1, wherein the audio-video instructions are part of a training sequence.

11. A medication administration confirmation method, comprising providing a user feedback on how to properly administer medication in accordance with a sequence of interactive instruction steps indicative of proper medication administration employing a medication administration apparatus, as the user attempts to administer medication before an image capture device, wherein providing the user feedback comprises:
  displaying one or more audio-video instructions on a display of a local computing device for instructing a user to properly administer the medication in accordance with the sequence of interactive instruction steps indicative of proper medication administration, at least one of the audio-video instructions instructing the user to follow one or more steps of the sequence of interactive instruction steps to properly position the medication administration apparatus relative to a user of the medication administration apparatus;
  capturing one or more audio-video sequences by a camera associated with the local computing device of the user administering medication following the display of the one or more audio-video instructions encouraging adherence to the sequence of interactive instruction steps including proper positioning of the medication administration apparatus for proper medication administration;
  in response to capturing the one or more audio-video sequences, automatically analyzing in real time, by a computer processor associated with the local device, motion of the user and/or the medication administration apparatus within at least one of the captured audio-video sequences to confirm that the user has properly administered the medication in accordance with the sequence of interactive instruction steps employing the medication administration apparatus;
  determining, from the analysis, that the user has not followed one or more steps of the sequence of interactive instruction steps, and that medication has not been properly administered; and
  responsive to determining that the medication has not been properly administered, outputting to the display while the user is administering the medication an additional one or more of the audio-video instructions to the user to encourage following of the one or more steps of the sequence of interactive instruction steps to confirm proper administration of the medication.

12. The method of claim 11, further comprising outputting to the display a prompt to the user to perform a particular sequence of actions in real time in response to the displayed audio video instructions to be stored as the one or more audio-video sequences.

13. The method of claim 12, wherein the particular sequence of actions is designed to assist in determining proper medication administration.

14. The method of claim 13, wherein the particular sequence of actions in response to the displayed audio-video instructions further comprises:
  displaying a medication administration apparatus;
  positioning the medication administration apparatus; and
  administering the medication.

15. The method of claim 11, further comprising transmitting from the local device one or more of the at least one audio-video sequences to a remote location for analysis.

16. The method of claim 15, further comprising receiving further information indicative of whether the user has properly administered the medication following the displayed audio-video instructions from the remote location.

17. A medication training method, comprising
  providing a user feedback on how to properly administer medication in accordance with a sequence of interactive instruction steps indicative of proper medication administration employing a medication administration apparatus, as the user attempts to administer medication before an image capture device, wherein providing the user feedback comprises:
  displaying on a display of a local computing device one or more training audio-video instructions comprising a sequence of medication administration instructions for training a user to properly administer a medication in accordance with the sequence of interactive instruction steps indicative of proper medication administration, at least one of the training audio-video instructions instructing the user to follow one or more steps of the sequence of interactive instruction steps to properly position the medication administration apparatus relative to a user of the medication administration apparatus;
  capturing by the image capture device of the local computing device one or more audio-video sequences of each step of the user administering training medication via a medication administration training apparatus following the display of the one or more training audio-video instructions encouraging adherence to the sequence of interactive instruction steps including proper positioning of the medication administration apparatus for proper medication administration;
  in response to capturing the one or more audio-video sequences, automatically analyzing in real time by a computer processor associated with the local device motion of the user and/or the medication administration apparatus within of at least one of the captured audio-video sequences of at least one medication administration training step to confirm that the user has properly performed the at least one medication administration training step in accordance with the sequence of interactive instruction steps employing the medication administration apparatus;
  determining, from the analysis, that the user has not followed one or more steps of the sequence of interactive instruction steps, and that the medication has not been properly administered during the at medication administration step; and
  responsive to determining that the medication has not been properly administered, outputting to the display while the user is administering the training medication an additional one or more of the training audio-video instructions to the user to encourage following of the one or more steps of the sequence of interactive instruction steps to confirm proper administration of the medication.

18. The method of claim 17, wherein the training medication to be administered via the medication administration training apparatus is an inhalable medication.

19. The method of claim 18, wherein analyzing at least one of the audio-video sequences comprises determining whether the inhalable medication training apparatus is properly positioned and oriented.

20. The method of claim 17, wherein the medication to be administered via the medication administration training apparatus is an injectable medication.

21. The method of claim 20, wherein analyzing at least one of the audio-video sequences comprises determining whether the injectable medication training apparatus is properly positioned and oriented.

22. The method of claim 17, further comprising outputting to the display a prompt to the user as to where and how to position the medication administration training apparatus in accordance with the one or more training audio-video instructions during performance of the one or more audio-video sequences.

23. The method of claim 17, further comprising transmitting at least one of the captured audio-video sequences to a remote location for further analysis.

24. The method of claim 17, further comprising notifying one or more of an administrator and the user responsive to determining that the user has not properly administered the training medication.

25. The medication confirmation apparatus of claim 1, wherein the one or more audio-video instructions comprise interactive instructions that allow the user to selectively view additional information regarding administering the medication.

26. The method of claim 11, wherein the one or more audio-video instructions comprise interactive instructions that allow the user to selectively view additional information regarding administering the medication.

27. The method of claim 17, wherein the one or more audio-video instructions comprise interactive instructions that allow the user to selectively view additional information regarding administering the medication.

* * * * *

UNITED STATES PATENT AND TRADEMARK OFFICE
CERTIFICATE OF CORRECTION

PATENT NO. : 9,875,666 B2
APPLICATION NO. : 13/235387
DATED : January 23, 2018
INVENTOR(S) : Adam Hanina, Gordon Kessler and Lei Guan It is certified that error appears in the above-identified patent and that said Letters Patent is hereby corrected as shown below:

In the Claims

Column 20, Line 41: In Claim 17, after "within" delete "of".

Column 20, Line 51: In Claim 17, delete "the at" and insert -- at the --, therefor.

Signed and Sealed this
Eighth Day of May, 2018

Andrei Iancu
*Director of the United States Patent and Trademark Office*